US006843780B2

(12) United States Patent
Larrain et al.

(10) Patent No.: US 6,843,780 B2
(45) Date of Patent: Jan. 18, 2005

(54) VALVE ARRANGEMENT

(75) Inventors: Ignacio Larrain, Lausanne (CH); Michael Jedwab, Lausanne (CH)

(73) Assignee: Nestec S.A., Vevey (CH)

(*) Notice: Subject to any disclaimer, the term of this patent is extended or adjusted under 35 U.S.C. 154(b) by 156 days.

(21) Appl. No.: 10/198,474

(22) Filed: Jul. 17, 2002

(65) Prior Publication Data

US 2003/0017068 A1 Jan. 23, 2003

Related U.S. Application Data

(63) Continuation of application No. PCT/EP01/00450, filed on Jan. 17, 2001.

(30) Foreign Application Priority Data

Jan. 20, 2000 (GB) ............................................. 0001309

(51) Int. Cl.[7] .......................... A61M 5/14; F16K 15/00; F16K 17/00; F16K 21/04; F16K 15/14
(52) U.S. Cl. .......................... 604/80; 604/256; 137/512
(58) Field of Search .............................. 604/27, 30, 34, 604/80, 81, 82, 83, 85, 89, 90, 246, 249, 251, 256; 137/512, 859

(56) References Cited

U.S. PATENT DOCUMENTS

| | | | |
|---|---|---|---|
| 3,119,411 A | * | 1/1964 | Bock et al. .................. 137/855 |
| 4,210,173 A | | 7/1980 | Choksi et al. ............ 137/512.3 |
| 4,573,974 A | * | 3/1986 | Ruschke ....................... 604/81 |
| 4,729,401 A | * | 3/1988 | Raines ........................ 137/512 |
| 5,354,272 A | | 10/1994 | Swendson et al. ............ 604/65 |
| 5,356,375 A | | 10/1994 | Higley .......................... 604/30 |
| 5,738,662 A | | 4/1998 | Shannon et al. ............ 604/247 |
| 5,961,488 A | | 10/1999 | Barak ........................... 604/80 |
| 6,042,564 A | | 3/2000 | Barak ......................... 604/151 |

FOREIGN PATENT DOCUMENTS

DE       19643360       5/1998

* cited by examiner

Primary Examiner—Nicholas D. Lucchesi
Assistant Examiner—Mark K. Han
(74) Attorney, Agent, or Firm—Winston & Strawn LLP

(57) ABSTRACT

A valve arrangement is described for providing clinical nutrition. The arrangement comprises a split flushing valve. Also described are a method of production of the valve arrangement, use of the valve arrangement in providing nutrition to a patient and a method of treatment of a patient that comprises administering an effective amount of a composition via the valve arrangement.

12 Claims, 3 Drawing Sheets

VALVE ARRANGEMENT

CROSS-REFERENCE TO RELATED APPLICATIONS

This application is a continuation of the U.S. national stage designation of International Application PCT/EP01/00450 filed Jan. 17, 2001, the entire content of which is expressly incorporated herein by reference thereto.

TECHNICAL FIELD

The present invention relates to a valve arrangement for providing clinical nutrition, a flow set comprising the valve arrangement, a method of production of the valve arrangement, use of the valve arrangement in providing nutrition to a patient and a method of treatment of a patient that comprises administering an effective amount of a composition via the valve arrangement.

BACKGROUND ART

Systems for administration of fluids to a patient are widely known. The manner of propelling the fluid to the patent may be by gravitation, by means of pressure applied on a deformable container, or by means of a pump. In pump-operated administration systems, the pump must be capable of administering the fluid in a controlled, continuous manner.

Pumps are employed to meet the need for a high degree of accuracy in the administration of fluids, to protect the patient and to maximize the effectiveness of medication.

WO98/46293 discloses the administration of two fluids to a patient. According to this document, a flow set is described which enables sequential administration of two fluids from a pair of containers to a patient. The flow set has a pair of valve assemblies each in communication with a container. Each valve assembly has a chamber; an inlet port sealed with a first one-way valve allowing flow of fluid through it only into the chamber; an outlet port being sealed with a second one-way valve allowing flow of fluid through it only out of the chamber; and a pump port located between the one-way valves. Inlet tubes connect a container to the inlet ports of each valve assembly. A connecting tube connects the pump ports of the valve assemblies to a pump. Outlet tubes are connected to the outlet port of each valve assembly for delivery of the two fluids to a patient. By reversing the pumping direction of the pump, fluid can be sequentially drawn from one container or the other. Generally, a sensor is associated with the pump for sensing when the containers are empty so that when no fluid passes the sensor the pump is switched off and an alarm sounds to alert an operator to the fact that more fluid is required.

This arrangement works well, but it has been found that it suffers from the problem that air entrained in the fluid can be released from solution and sensed by the sensor. This can result in activation of the alarm and switching off of the pump even when more fluid is not required. This is inefficient. Indeed, when the alarm sounds, it generally indicates a) the container is empty and more fluid is required or b) feeding is finished and no more fluid is necessary for this feeding. Thus, when entrained air falsely trips the alarm (often referred to as a nuisance alarm), a nurse may either a) believe that she must renew the fluid supply as more fluid is required or b) falsely believe feeding is finished and no more fluid is required or c) have the experience and sense to check the fluid supply, realize it was only a nuisance alarm and re-start the pump with the same fluid supply (preferably shaking to remove any air bubbles).

Therefore, a need exists for a valve assembly which achieves a good flow and which can be used in the efficient administration of two fluids to a patient, which is safe, relatively simple, easy to use, and requires a single pump. Furthermore, there is a need for a solution to the problem of unnecessary switching off of the pump and activation of the alarm.

The present invention addresses and resolves the problems of the art.

SUMMARY OF THE INVENTION

Remarkably, it has now been found that if a critical distance is maintained between the pump port and the inlet valve more efficiency can be achieved and unnecessary switching off of the pump and activation of alarms can be avoided.

Consequently, in a first aspect, the present invention provides a valve arrangement having a chamber and three ports which include an inlet port sealed with a first one-way valve allowing flow of fluid through it only into the chamber, an outlet port sealed with a second one-way valve allowing flow of fluid through it only out of the chamber and a pump port located between the one-way valves, wherein the first one-way valve is not directly adjacent the pump port.

In a second aspect the invention provides a flow set for the sequential administration of two fluids from a pair of containers to a patient which comprises two valve arrangements according to an embodiment of the invention; a pair of inlet tubes for connecting containers to the inlet port of each valve arrangement; connecting tubes for connecting a pump to the pump ports; and a pair of outlet tubes for connecting the outlet of each valve arrangement for the delivery of two fluids to a patient.

In a third aspect the invention provides a method of production of the valve arrangement which comprises making a chamber, making three ports including an inlet port, an outlet port and a pump port, fixing a first one way valve adjacent the inlet port and not directly adjacent the pump port for allowing fluid only into the chamber and fixing a second one-way valve adjacent the outlet port for allowing fluid only out of the chamber.

In a forth aspect the invention provides use of a valve arrangement according to an embodiment of the invention for providing nutrition to a patient.

In a fifth aspect the invention provides a method of treatment of a patient that comprises administering an effective amount of a fluid via a valve arrangement according to an embodiment of the invention.

BRIEF DESCRIPTION OF THE DRAWING FIGURES

Additional features and advantages of the present invention are described in, and will be apparent from, the description of the presently preferred embodiments which are set out below with reference to the drawings in which.

DETAILED DESCRIPTION OF THE PREFERRED EMBODIMENTS

Figure 1:
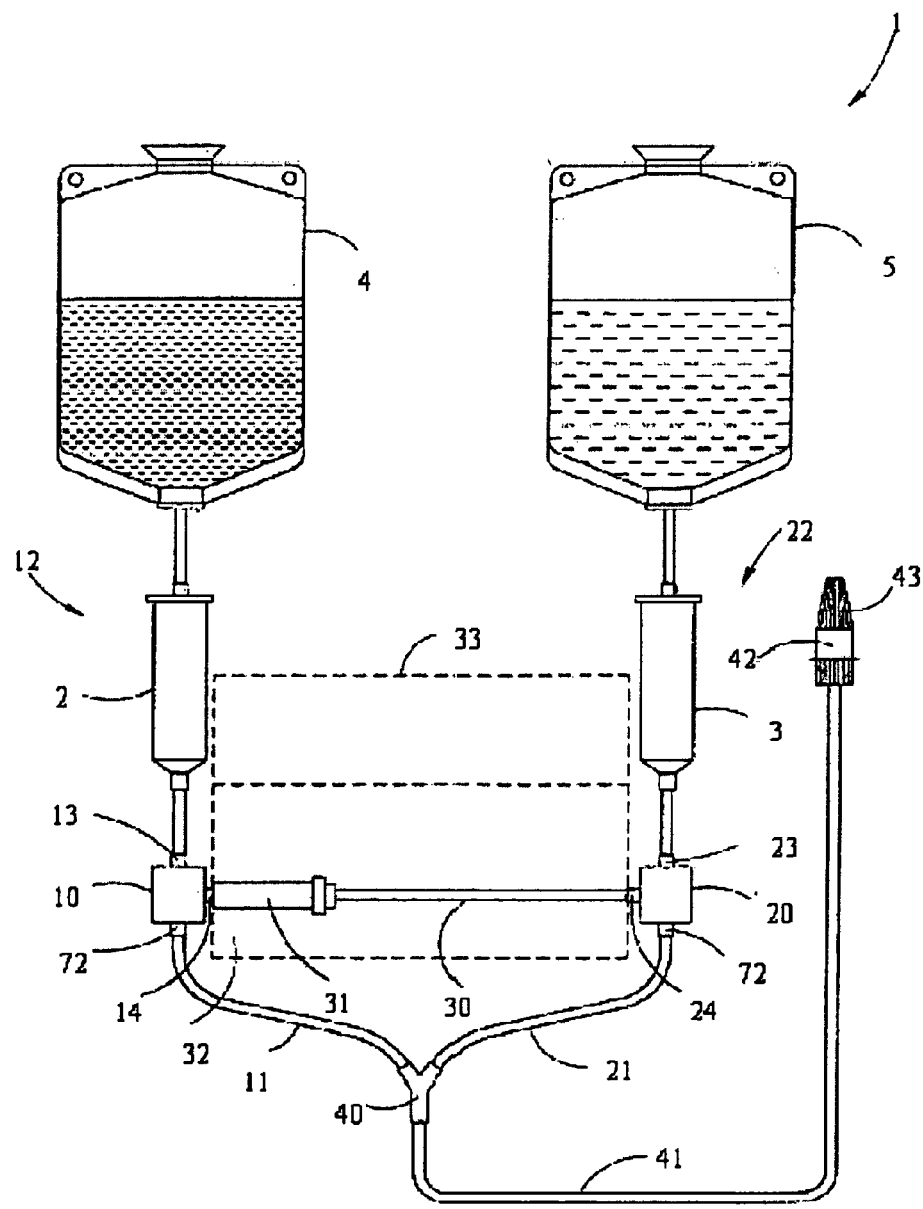
FIG. 1 shows a flow set having a known valve assembly.

A valve arrangement according to an embodiment of the invention provides the advantage of permitting simple and safe switching between fluids from two containers to which a flow set is connected. Fluid may be drawn from one container, into an embodiment of the valve assembly and out through its pump port to a second embodiment of a valve assembly through its pump port. Fluid may flow out of the outlet port of the second valve assembly to a patient. By merely reversing the pumping direction a fluid may be drawn from a second container into the second embodiment of the valve assembly and hence to a patient in a manner mirroring the first. No disconnection of tubing is required and no manual adjustment of valves is required.

Another advantage of the present invention is that the flow of fluid from the outlet port of the valve arrangement can be accurately controlled. In view of the fact that the pump port is not directly adjacent the inlet one-way valve, any air released from solution does not enter the pump port. Consequently, air is not sensed by a sensor associated with the pump and unnecessary triggering of alarms and switching off of the pump can be avoided. Known valve arrangements have suffered from the problem that they have been prone to developing an air trap here and this has inhibited their efficiency.

Yet another advantage of the present invention is that it provides an arrangement that is easier and less expensive to make than known arrangements. Standard commercially available parts eg valves can be employed. In addition, a simple construction method can be carried out from available parts comprising a simple housing and membranes and this increased simplicity adds to the speed at which production can be achieved. With regard to the fluid flow, two liquids can be administered to a patient with no cross contamination. Advantageously this can be carried out with a single pump to manage two fluids.

In addition, the switching between fluids may be rapid because no disconnection of tubing or changing of pumps is required. Furthermore, two separate fluids can be managed independently with regard to volume and flow rate. Preferably, these fluids include a nutritional composition for the patient.

Preferably, an embodiment of a valve arrangement according to the present invention includes a distance of about 20 cm to about 60 cm between the axis of the pump port and the surface of the inlet one-way valve. More preferably the distance is about 30 cm to about 50 cm. Most preferably the distance is about 40 cm.

Remarkably, it has now been found that these specific distances are critical to the efficiency of the valve arrangement. They are not merely a result of optimization of the known apparatus. Mere optimization would be expected to lead to no distance. In contrast, it has surprisingly been found that the distances help ensure that an air trap does not inhibit the smooth flow of fluid.

Preferably, the inlet valve has a low cracking pressure and the outlet valve has a high cracking pressure. More preferably, the cracking pressure of the inlet valve is close to and is approximately 0 kPa. More preferably, the cracking pressure of the outlet valve exceeds about 10 kPa. More preferably it exceeds about 15 kPa.

It has been found that these cracking pressures provide the advantage that, if a pump is disconnected from the valve arrangement fluid is not able to pass through the outlet valve to a patient. Therefore, uncontrolled flow to the patient is prevented.

Preferably the chamber has an internal diameter of about 1 mm to about 5 mm. More preferably it is about 2 mm to about 4 mm. Most preferably it is about 3 mm. Preferably it is provided by tubing having this internal diameter.

It has suprisingly been found that these specific internal diameters give rise to the advantage that less dissolved air is present in the chamber compared to known valve arrangements. In the light of this the air does not come out of solution and form an air pocket.

Preferably, an embodiment of a valve arrangement according to the present invention includes a valve which comprises a flexible membrane which is deformable under pressure in a desired flow direction. Each flexible membrane has perforations through it which open at a selected extent of deformation of the flexible membrane to permit flow. Each valve assembly may be provided with a support 80 associated with each flexible membrane for preventing the flexible membrane from deforming sufficiently in a direction opposite the flow direction for preventing back flow. In accordance with a preferred embodiment the invention the membrane of the inlet valve deforms at a low cracking pressure and the membrane of the outlet valve deforms at a high cracking pressure.

Preferably, an embodiment of a valve arrangement according to the present invention is obtained by modification of known apparatus. Suitable starting materials are for example: a housing manufactured of metal or plastics material, preferably rigid plastics material including ABS, polycarbonate, PVC, acrylic or MABS; and a valve membrane manufactured of a resilient material including polyurethane, silicon or rubber.

Preferably, a method of treatment according to the present invention includes the steps of sequentially administering two fluids from a pair of containers to a patient using a pump to propel the fluids and a valve arrangement according to an embodiment of the invention by:

operating a pump in one pumping direction for pumping fluid from a first container through a pump system, the fluid flowing in a first flow path through an inlet tube connected to the first container to the inlet port of a first valve assembly, out through the pump port of the first valve assembly, in the pump port of the second valve assembly, and through an outlet tube to a patient; and reversing the pumping direction of the pump for pumping fluid from the second of the containers in a second flow path through an inlet tube connected to a second container to the inlet port of the second valve assembly, out through the pump port of the second valve assembly and in the pump port of the first valve assembly, and through an outlet tube to a patient.

Preferably the pumping direction of the pump is reversed automatically in accordance with instructions stored within a control unit associated with the pump. The pumping direction is preferably reversed at least twice.

A known flow set which may be used to sequentially administer two fluids is illustrated for comparison with the invention in FIG. 1. The flow set 1 is made up of a tubing set comprising a pair of tube branches. Each branch has a drip chamber 2, 3, and a valve arrangement 10, 20. The valve arrangements are connected together by a connecting tube 30. A pair of outlet tubes 11, 21, one for each branch, is connected to the valve arrangement at one of their ends and they are connected together at their other end by a Y connector 40. The connecting tube 30 is positioned upstream of Y-connector 40. An administration tube 41 is connected to the Y connector at one end and its other end is connected to a connector 42. As is conventional, the connector 42 may be connected to a catheter, an enteral feeding tube, etc. When not in use, the free end of the connector 42 is covered by a cover 43.

Each tube branch is made up of a pair of inlet tubes 12, 22 and a pair of outlet tubes 11, 21. One end of each inlet tube 12, 22 is connectable to a separate fluid container 4, 5. The other end of each inlet tube 12, 22 is connected to an inlet 13, 23 of a valve arrangement 10, 20. Drip chambers 2, 3 are provided in series with the inlet tubes 12, 22. One end of each outlet tube 11, 21 is connected to the Y-connector 40. A connecting tube 30 spans between the two valve arrangements 10, 20; connecting to a pump port 14, 24 of each valve arrangement 10, 20. A shaped connecting element 31 is provided in series with the connecting tube 30.

Figure 2:
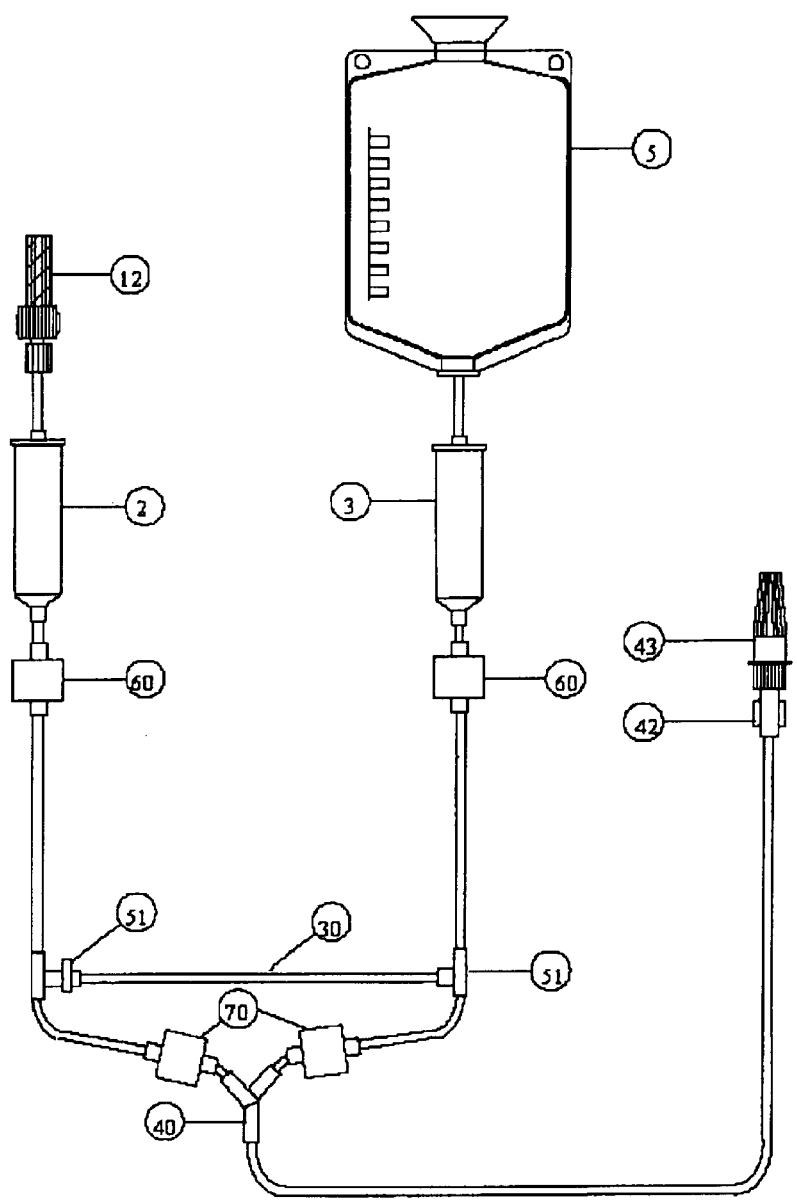
FIG. 2 shows a flow set having a valve assembly according to an embodiment of the invention.
Figure 3:
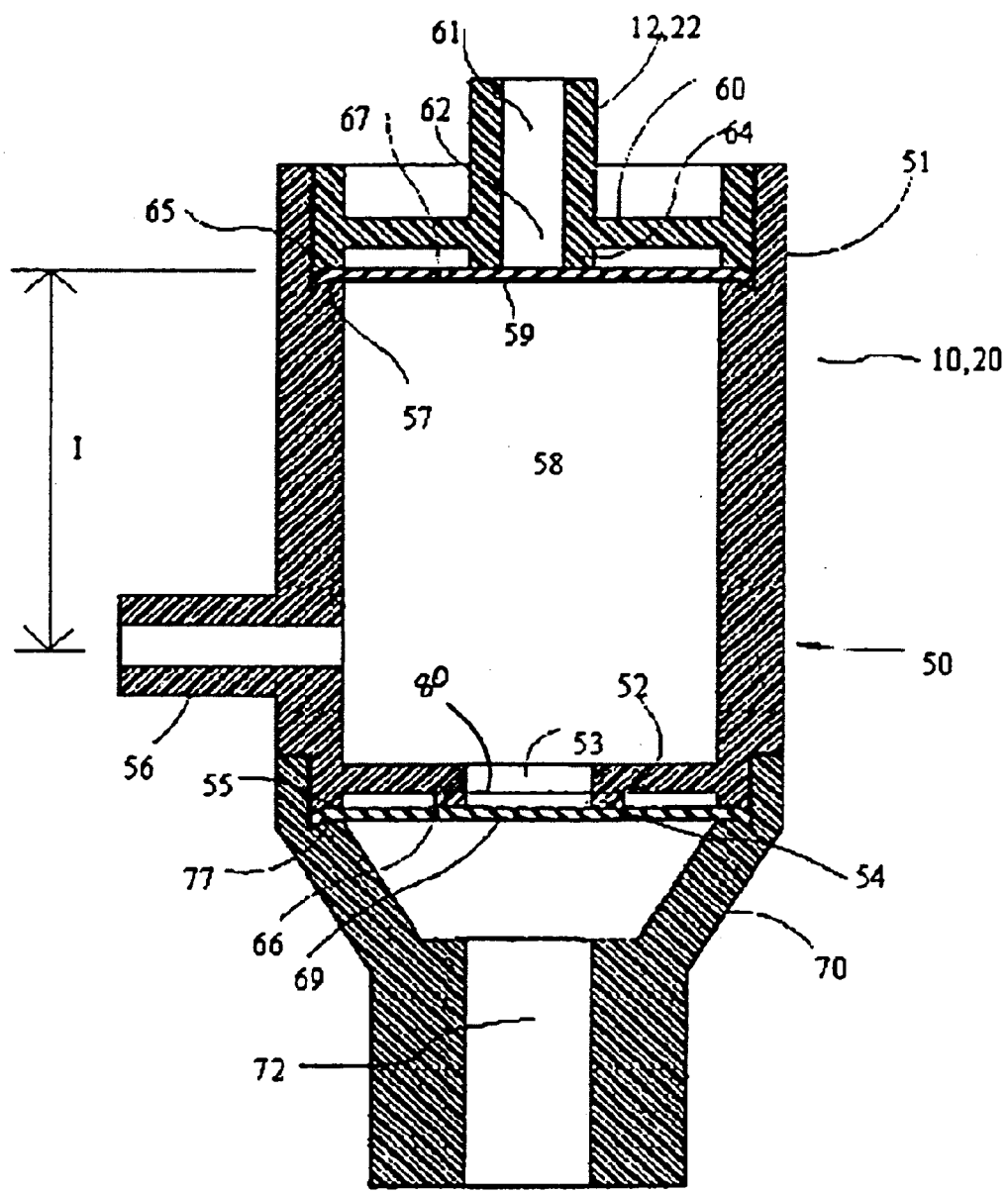
FIG. 3 shows a valve arrangement in accordance with the invention.

Referring now to FIGS. 2 and 3, each valve arrangement 10, 20 according to an embodiment of the invention comprises a housing 50 formed of three body members; a first body member 51, a second body member 60 and a third body member 70.

The first body member 51 comprises a channel having a chamber 58 at one end. The lower end of the chamber is closed by a base plate 52 which has an opening 53 having an annular rim 54 that projects downwards. An annular projection 55 projects from the periphery of the lower end of the base plate 52. A lateral pump port 56 is provided in a side wall of the chamber and a connecting tube 30 can be connected to this port. An annular shoulder 57 is located atop the chamber around its inner surface.

The second body member 60 is sized so that at least a lower portion of it fits snugly into an opening atop the first body member 51 to abut the shoulder and form a seal with chamber 58. The second body member 60 has an annular projection 65 projecting downwards from its lower end. The annular projection 65 has a shape that is complementary to the annular shoulder 57 of the first body member 51. In this way, when the second body member 60 is fitted into the first body member 51, the annular shoulder 57 and the annular projection 65 form an annular clamp. It will be appreciated that the shoulder 57 and the projection 65 could be reversed. A flexible membrane 59 is clamped between the annular shoulder 57 and the annular projection 65. The distance (I) between the top surface of this flexible membrane 65 and the central axis of the pump port 56 is at least about 20 cm. This helps ensure that an air pocket does not pass into the pump port and to a pump where it may be detected by a sensor associated with the pump.

An opening 61 in the upper surface of the second body member 60 provides an inlet port and an inlet tube 12, 22 may extend from this port. An opening 62 in the lower surface of the second body member 60 has an annular rim 64 which projects into the chamber 58.

The third body member 70 is in the form of a channel. An annular shoulder 77 is provided atop the third body member 70 around its inner surface. The annular shoulder 77 has a shape complementary to the lower end of the annular projection 55 of the first body member 51. In this way, when the first body member 51 abuts the third body member 70, the annular projection 55 and the annular shoulder 77 form an annular clamp. It will be appreciated that the annular shoulder 77 and the projection 55 could be reversed. Further, the annular projection 55 of the first body member 51 is sized to fit snugly in the bore of the third body member 70 to form a seal. A flexible membrane 69 is clamped between the annular projection 55 of the first body member 51 and the annular shoulder 77 of the third body member 70. A lower opening 72 in the third body member 70 provides an outlet from which an outlet tube 11, 21 may extend.

In an alternative embodiment, for example as shown in FIG. 2, the chamber may include tubing. The first body member may include a chamber which has and inlet port, an outlet port, and a pump port. The second body member may hold a first flexible membrane and it may be connected via tubing to the first body member. The third body member may hold a second flexible membrane and it may be connected via tubing to the first body member.

The two flexible membranes 59, 69 are made of a resilient flexible material, typically a sterilisable material such as silicon, rubber or any other suitable material. The membranes each have a plurality of slits (for example two) which, in the rest state, are closed and do not permit flow of fluid. Typically, the membranes 69 are designed so that their slits 66 will open only when the pressure differential over the membrane exceeds about 20 kPa. This prevents undesired free flow of the fluid from the containers 4, 5, which in a clinical setting are typically placed on a stand of a height of about 1.5 metres. Typically, the membranes 59 are designed so that their 67 slits will open under a small pressure differential of about 0 kPa.

A pump 32 of a pump unit 33 is coupled to the connecting tube 30. The pump 32 is preferably a peristaltic pump but any pump which is able to pump fluid at controlled flow rates in both directions and which is suitable for clinical applications may be used. The pump unit 33 may include a control unit 34. The control unit 34 typically comprises a control panel which has a display and a key pad. The key pad may be used for manual control of the pump, data entry, and the like. The control unit may include a microprocessor for controlling and activating the pump. A memory may be associated with, or be incorporated in, the microprocessor. If desired, the control unit may include an audio, visual or dual alarm signalling means.

The pump unit 33 has a socket which is complementary to the shaped connecting element 31. When the pump system is correctly assembled, the shaped element 31 fits into the socket in the pump unit 33. The pump unit 33 may be provided with a micro switch in the socket which generates a signal when the shaped connecting element 31 is fitted in the socket. This signals to the control unit that the pump system has been correctly assembled. The control unit may be programmed not to initiate the pump 32 unless the correct signal has been received.

The flow set 1 is typically mounted on a stand with the containers 4 and 5 being held by an arm at the top of the stand.

Drip chambers 2, 3 may be provided adjacent the outlets 72 of the valve arrangements 10, 20 or between the containers and the inlets of the valve arrangements.

In use, pump 32 pumps fluid from one of the containers 4 or 5 to a patient. For example, the pump 32 draws fluid from the left hand container 4 of FIG. 2. The fluid is drawn into the inlet tube 12, through the drip chamber 2, and into the inlet 61 of the valve arrangement 10.

Prior to pumping by the pump 32, the flexible membranes 59, 69 are in the rest state. When fluid is drawn through the inlet tube 12, the flexible membrane 59 is stretched. Once a selected small threshold pressure differential is reached and the first flexible membrane 59 is sufficiently stretched, it deforms and slits in the membrane 59 widen and open to allow flow of fluid from the inlet tube 12 into the chamber 58.

Simultaneously, the suction of the pump 32 reduces the pressure in the pump port, in the connecting tube 30 and in the chamber 58. This causes the second flexible membrane 69 to seal against the annular rim of base plate 52 of the first body member 51. Fluid flows from the chamber 58 through the pump port 56 and into the connecting tube 30. Fluid is unable to penetrate through the second flexible membrane 69.

Fluid is propelled by the pump 32 along the connecting tube to the chamber of a second valve arrangement 20. Fluid enters the valve arrangement 20 through its lateral pump port 56. Once in the chamber 58 of a second valve arrangement, the fluid pressure forces the first flexible membrane 59 for the valve arrangement upwards against the annular rim of second body member 60. This membrane cannot deflect sufficiently to permit fluid flow through it. However, when the positive pressure induced in the chamber 58 by the pump 32 reaches a pressure of at least about 20 kPa it causes the second flexible membrane 69 to stretch and deform. Once the selected threshold pressure differential is reached and the second flexible membrane 69 is sufficiently stretched, slits in the membrane 69 widen and open to allow flow of fluid from the chamber 58 out of the outlet port 72 to outlet tube 21.

The fluid flows through the outlet tube 21, through a Y-connector 40, and into an administration tube 41. A small amount of fluid may initially flow into the left-hand second tubing element 11 but it is prevented from entering the first valve arrangement 10 by the second flexible membrane 69 of this valve arrangement.

Administration of a second fluid is achieved by reversing the pumping direction of the pump 32. The pumping direction of the pump 32 may be reversed manually or automatically at selected times by a control unit.

The system provides a safe and rapid means of sequentially administering two fluids to a patient which is extremely simple to operate.

It will be appreciated that numerous modifications may be made to the preferred embodiments by one of ordinary skill I the art. For example, it is not essential for drip chambers 2, 3 to be connected in the flow set 1. It is also not essential to provide the pump 32 with a socket and the connecting tube 30 with a shaped connecting element 31. Similarly, the Y-connector 40 may be replaced with any suitable connector. Similarly, the flow set need not use the membrane type valves described above. Other valves may be used; for example each valve may be replaced with a one way valve which opens upon the correct threshold pressure being reached. The connecting tube 30 may then extend from a position between the pair of one way valves of each assembly. These and other modifications and variations that do not depart from the spirit and scope of the invention form part of the subject matter that is set forth in the following claims.

What is claimed is:

1. A valve arrangement having a chamber and three ports, including an inlet port that includes a first one-way valve for allowing flow of fluid through it and only into the chamber, an outlet port that includes a second one-way valve for allowing flow of fluid through it and only out of the chamber, and a pump port located between the one-way valves, wherein the first one-way valve is not directly adjacent the pump port, the first one-way valve is sealed to the inlet port, the second one-way valve is sealed to the outlet port, and the axis of the pump port and the surface of the inlet one-way valve are separated by a distance of about 20 cm to about 60 cm.

2. The valve arrangement of claim 1, wherein the inlet valve has a low cracking pressure which is close to 0 kPa and the outlet valve has a high cracking pressure which exceeds 10 kPa.

3. The valve arrangement of claim 1, wherein the chamber has an internal diameter of about 1 mm to about 5 mm.

4. The valve arrangement of claim 1, wherein at least one of the valves comprises a flexible membrane which is deformable under pressure in a desired flow direction.

5. The valve arrangement of claim 4, wherein the flexible membrane has perforations through it which open at a selected extent of deformation of the flexible membrane to permit flow.

6. The valve arrangement of claim 4, wherein the valve may be provided with a support associated with each flexible membrane for preventing the flexible membrane from deforming sufficiently in a direction opposite the flow direction for preventing back flow therethrough.

7. A flow set for the sequential administration of two fluids from a pair of containers to a patient which comprises two valve arrangements according to claim 1, each one operatively associated with a container.

8. The valve arrangement of claim 7, wherein each inlet valve has a low cracking pressure which is close to 0 kPa and each outlet valve has a high cracking pressure which exceeds 10 kPa.

9. The valve arrangement of claim 7, wherein each chamber has an internal diameter of about 1 mm to about 5 mm.

10. The valve arrangement of claim 7, wherein at least one of the valves comprises a flexible membrane which is deformable under pressure in a desired flow direction.

11. The valve arrangement of claim 10, wherein the flexible membrane has perforations through it which open at a selected extent of deformation of the flexible membrane to permit flow.

12. The valve arrangement of claim 10, wherein the valve may be provided with a support associated with each flexible membrane for preventing the flexible membrane from deforming sufficiently in a direction opposite the flow direction for preventing back flow therethrough.

* * * * *